(12) United States Patent
Haibara et al.

(10) Patent No.: US 8,575,571 B2
(45) Date of Patent: Nov. 5, 2013

(54) CLEANING APPARATUS, MEASUREMENT METHOD AND CALIBRATION METHOD

(75) Inventors: Teruo Haibara, Hikari (JP); Yoshihiro Mori, Shunan (JP); Etsuko Kubo, Hikari (JP); Masashi Uchibe, Hikari (JP)

(73) Assignee: Siltronic AG, Munich (DE)

( * ) Notice: Subject to any disclaimer, the term of this patent is extended or adjusted under 35 U.S.C. 154(b) by 0 days.

(21) Appl. No.: 13/618,624

(22) Filed: Sep. 14, 2012

(65) Prior Publication Data
US 2013/0112900 A1 May 9, 2013

(30) Foreign Application Priority Data

Nov. 4, 2011 (JP) ................. 2011-242129

(51) Int. Cl.
*G01J 1/58* (2006.01)
(52) U.S. Cl.
USPC ............ 250/459.1; 250/252.1; 250/458.1
(58) Field of Classification Search
USPC ................. 250/252.1, 458.1, 459.1
See application file for complete search history.

(56) References Cited

U.S. PATENT DOCUMENTS

| | | |
|---|---|---|
| 5,144,831 A | 9/1992 | Hale et al. |
| 2006/0061225 A1 | 3/2006 | Beck et al. |

FOREIGN PATENT DOCUMENTS

| | | |
|---|---|---|
| EP | 0860866 A1 | 8/1998 |
| EP | 1645342 A1 | 4/2006 |
| JP | 3176640 A | 7/1991 |
| JP | 2000350282 A | 12/2000 |

OTHER PUBLICATIONS

Pickworth et al., Studies of the cavitational effects of clinical ultrasound by sonoluminescence: 2. Thresholds for sonoluminescence from a therapeutic ultrasound beam and the effect of temperature and duty cycle, Phys. Med. Biol., 1988, vol. 33, No. 11, 1249-1260.

*Primary Examiner* — Mark R Gaworecki
(74) *Attorney, Agent, or Firm* — Leydig, Voit & Mayer, Ltd.

(57) ABSTRACT

A calibration method for calibrating a measurement device for measuring a concentration of a gas dissolved in a liquid includes varying the concentration of the gas dissolved in the liquid, and predetermining, as a reference concentration, a concentration of the gas at which an intensity of luminescence produced when the liquid is irradiated with ultrasonic waves shows a peak. The liquid is illuminated with ultrasonic waves while varying the concentration of the gas in the liquid and a measured value is measured, using the measurement device, as a concentration of the gas in the liquid when the intensity of the luminescence shows a peak. The measurement device is calibrated based on the measured value and the reference concentration.

7 Claims, 4 Drawing Sheets ived invention will be described in even greater
CLEANING APPARATUS, MEASUREMENT METHOD AND CALIBRATION METHOD

CROSS-REFERENCE TO PRIOR APPLICATION

Priority is claimed to Japanese Patent Application No. JP 2011-242129, filed on Nov. 4, 2011, the entire disclosure of which is hereby incorporated by reference herein.

FIELD

This invention relates to a cleaning apparatus, a measurement method, and a calibration method, and more specifically to an apparatus for cleaning a substrate, a method for measuring a concentration of a dissolved gas, such as dissolved nitrogen, in a cleaning liquid used in the cleaning apparatus, and a method for calibrating a measurement device used in the measurement method.

BACKGROUND

In a process for manufacturing substrates such as silicon wafers, a process for cleaning substrates such as a dip type or a single-wafer type has been conventionally performed, in order to remove from the substrates organic substances, metal impurities, particles (fine particles), native oxide film, and the like that may cause defects in semiconductor devices.

In such processes for cleaning substrates, various types of cleaning methods are used to suit their purposes. In particular, when foreign substances such as particles are removed by a dip type cleaning method, a method is used in which a substrate is dipped in a cleaning liquid contained in a cleaning tank, and the cleaning liquid in which the substrate is dipped is irradiated with ultrasonic waves having a frequency around 1 MHz, referred to as "megasonics". It is generally believed that the use of ultrasonic waves having a frequency around 1 MHz can increase the cleaning effect on submicron-size microparticles on the surface of a substrate, while reducing damage to the substrate.

The concentration of a gas dissolved in a cleaning liquid affects the removal efficiency for foreign substances such as particles. For example, when particles are removed from substrates by using ultrapure water as a cleaning liquid, and irradiating the ultrapure water with megasonics, the particle removal efficiency from the substrates is affected by the concentration of nitrogen dissolved in the cleaning liquid. More specifically, when the concentration of nitrogen dissolved in the cleaning liquid is within a prescribed range, the particle removal efficiency from the substrates is relatively high. Thus, theoretically, it is possible to effectively remove particles if the concentration of a dissolved gas such as the concentration of nitrogen dissolved in the cleaning liquid is monitored in the cleaning process, and the concentration of the gas dissolved in the cleaning liquid is controlled to be within a certain range.

Conventionally, a gas component contained in a fluid medium is introduced into a receptor through a polymer membrane, and the concentration of the gas component is calculated based on a change in thermal conductivity within the receptor (Japanese Patent Laying-Open No. 1991-176640). Thus, a method in which the concentration of nitrogen dissolved in a cleaning liquid is monitored using this measurement method is being conducted.

SUMMARY

In an embodiment, the present invention provides a calibration method for calibrating a measurement device for measuring a concentration of a gas dissolved in a liquid. The method includes varying the concentration of the gas dissolved in the liquid, and predetermining, as a reference concentration, a concentration of the gas at which an intensity of luminescence produced when the liquid is irradiated with ultrasonic waves shows a peak. The liquid is illuminated with ultrasonic waves while varying the concentration of the gas in the liquid and a measured value is measured, using the measurement device, as a concentration of the gas in the liquid when the intensity of the luminescence shows a peak. The measurement device is calibrated based on the measured value and the reference concentration.

BRIEF DESCRIPTION OF THE DRAWINGS

The present invention will be described in even greater detail below based on the exemplary figures. The invention is not limited to the exemplary embodiments. Features described and/or represented in the various figures can be used alone or combined in embodiments of the present invention. Other features and advantages of various embodiments of the present invention will become apparent by reading the following detailed description with reference to the attached drawings which illustrate the following.

In the drawings, identical or corresponding parts are denoted by identical reference numbers, and description thereof may not be repeated for each drawing.

DETAILED DESCRIPTION

Figure 1:
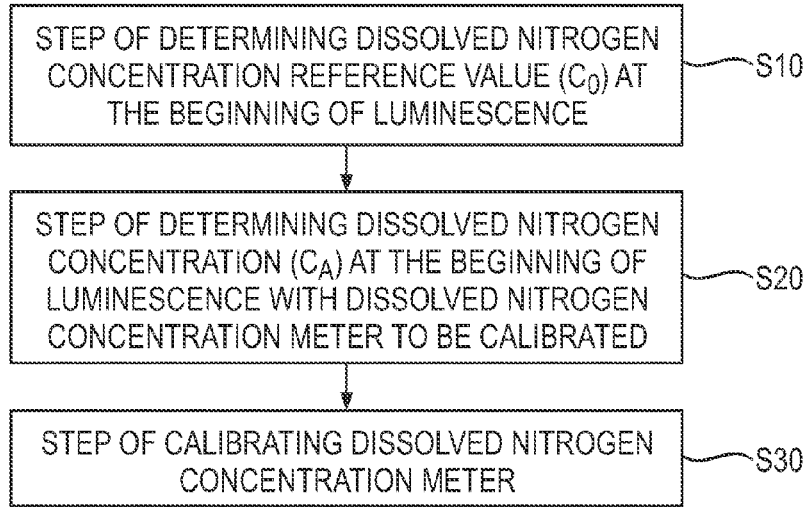
FIG. 1 is a flowchart showing a method for calibrating a dissolved nitrogen concentration meter according to an embodiment of the present invention.

The device for measuring the concentration of dissolved nitrogen based on the method of Japanese Patent Laying-Open No. 1991-176640 has problems with the stability of measurement precision, and therefore, is recommended to receive an annual calibration test conducted by the manufacturer. However, in view of the inventors' experience of using the device for measuring the concentration of dissolved nitrogen, errors in measured values increase from 20 to 40% in one year. For this reason, in order to accurately measure the concentration of dissolved nitrogen, it is necessary to calibrate the device with a frequency higher than that recommended by the manufacturer.

On the other hand, the method for calibrating the device for measuring the concentration of dissolved nitrogen performed by the manufacturer is a method in which a thermal conductivity sensor constituting the measurement device is calibrated by using pure nitrogen gas, and therefore, the calibration test is not conducted using the actual water containing dissolved nitrogen. Hence, it is difficult to calibrate the measurement device using the above-described method during running of a cleaning apparatus incorporating the device for measuring the concentration of dissolved nitrogen, or during intervals between cleaning steps. That is, it has conventionally been difficult to perform calibration of the device for measuring the concentration of dissolved nitrogen easily and frequently.

Therefore, in order to realize accurate measurement of the concentration of dissolved nitrogen, the present invention provides a method allowing a user of a measurement device to easily calibrate the device during running of a cleaning apparatus or during intervals between cleaning steps, for accurate measurement of the concentration of dissolved nitrogen. Further, finding such a calibration method is particularly advantageous since it will also lead to improved stability of measurement precision for a measurement device for measuring the concentration of a dissolved gas other than dissolved nitrogen.

Furthermore, in order to accurately and stably measure the concentration of a dissolved gas such as dissolved nitrogen as described above, a new method for measuring a concentration of a dissolved gas having excellent stability of measurement precision is provided.

By utilizing such a measurement method in which calibration of a device for measuring a concentration of a dissolved gas is frequently performed, or which has excellent stability of measurement precision, it will be possible to reliably clean substrates while keeping conditions for cleaning the substrates satisfactory.

In an embodiment, the invention solves the problems described above, and provides a cleaning apparatus capable of cleaning substrates effectively and stably, a method for calibrating a device for measuring a concentration of a dissolved gas used in the cleaning apparatus, and a method for measuring a concentration of a dissolved gas.

The inventors conducted detailed studies of the relation between a concentration of a gas dissolved in a liquid and a luminescence intensity of a luminescence phenomenon produced when the liquid is irradiated with ultrasonic waves (sonoluminescence), and consequently completed the present invention. That is, the inventors found that when the liquid is irradiated with ultrasonic waves while gradually increasing the concentration of a gas dissolved in the liquid from zero, the luminescence phenomenon abruptly occurs when a specific concentration of a dissolved gas has been reached. The inventors also found that subsequent further increase in the concentration of a dissolved gas causes the luminescence intensity to gradually decrease.

Moreover, as a result of the inventors' studies, it was found that the concentration of a dissolved gas at which the luminescence phenomenon occurs suddenly and abruptly as described above always shows a certain value when other conditions (for example, the frequency of ultrasonic waves with which the liquid is irradiated, the intensity of the ultrasonic waves (watt density), the type of ultrasonic transducer, the amount of liquid supplied, the liquid temperature, the size or shape (design) of the vessel holding the liquid, the internal structure of the vessel (for example, the placement of jigs installed within the vessel), etc.) are constant. By utilizing this phenomenon, it is possible to calibrate a measurement device for measuring the concentration of a dissolved gas, using, as a reference value, a concentration of a dissolved gas at which intense luminescence occurs suddenly and abruptly.

Based on this finding, a calibration method according to an embodiment of the invention is a calibration method for calibrating a measurement device for measuring a concentration of a gas dissolved in a liquid, which includes the following steps. That is, a step of varying the concentration of the gas dissolved in the liquid, and predetermining, as a reference concentration, a concentration of the gas at which an intensity of luminescence produced when the liquid is irradiated with ultrasonic waves shows a peak, is conducted. Next, a step of measuring the concentration of the gas in the liquid with the measurement device to be calibrated when the intensity of the luminescence shows a peak by irradiating the liquid with ultrasonic waves while varying the concentration of the gas in the liquid, to determine a measured value of the concentration of the gas, is conducted. A step of calibrating the measurement device to be calibrated based on the measured value and the reference concentration is conducted. In the predetermining step described above, any method capable of accurately measuring the concentration can be used as a method for measuring the concentration of the gas dissolved in the liquid. For example, in the predetermining step described above, a measurement device of the same type as the measurement device to be measured, having the setting at the time of shipment from the factory (namely, a measurement device capable of accurate measurement that has just been subjected to adjustment by the manufacturer) may be used.

In this way, the measurement device can be calibrated easily and accurately by utilizing sonoluminescence.

A measurement method according to an embodiment of the invention is a measurement method for measuring a concentration of a gas dissolved in a liquid, which includes the following steps. That is, a step of measuring an intensity of luminescence produced by irradiating the liquid to be measured with ultrasonic waves by way of a luminescence intensity measuring device to obtain a measured value of the intensity of the luminescence is conducted. A step of deriving the concentration of the gas from the measured value of the intensity of the luminescence based on a previously found correlation between the concentration of the gas dissolved in the liquid and the intensity of the luminescence produced when the liquid is irradiated with ultrasonic waves is conducted.

In this way, with respect to a range of concentrations of the gas having a correlation between the intensity of the luminescence due to sonoluminescence in the liquid and the concentration of the gas dissolved in the liquid, the concentration of the gas dissolved in the liquid can be easily found from the intensity of the luminescence.

A cleaning apparatus according to an embodiment of the invention is an apparatus for cleaning a substrate using the above-described measurement method, which includes a cleaning tank, an ultrasonic generating unit, a luminescence intensity measuring device, and a processing unit. The cleaning tank holds a cleaning liquid for cleaning the substrate. The ultrasonic generating unit is for irradiating the cleaning liquid with ultrasonic waves and generates ultrasonic waves. The ultrasonic generating unit is connected to the cleaning tank via a medium capable of transmitting ultrasonic waves to the cleaning liquid in the cleaning tank. The luminescence intensity measuring device measures the intensity of luminescence produced when the cleaning liquid is irradiated with ultrasonic waves. The processing unit derives a concentration of a gas dissolved in the cleaning liquid from a measured value of the intensity of the luminescence measured by the luminescence intensity measuring device and a previously found correlation between the concentration of the gas dissolved in the cleaning liquid and the intensity of the luminescence.

In this way, the concentration of the gas dissolved in the cleaning liquid can be accurately measured from the intensity of the luminescence due to sonoluminescence, thus enabling a characteristic (cleaning capability) of the cleaning liquid affected by the gas concentration in the cleaning liquid to be accurately grasped. Moreover, the characteristic of the cleaning liquid can be kept satisfactory by adjusting the cleaning liquid such that the gas concentration is within an appropriate range.

According to the present invention, it is possible to accurately and easily calibrate a measurement device for measuring a concentration of a gas dissolved in a liquid, by utilizing sonoluminescence in the liquid. It is also possible to accurately measure the concentration of the gas dissolved in the liquid by utilizing sonoluminescence in the liquid.

First Embodiment

Referring to FIGS. 1 to 5, a calibration method for calibrating a dissolved nitrogen concentration meter according to the present invention will be described. The calibration method according to the present invention is specifically a method for calibrating a dissolved nitrogen concentration meter, which is monitoring means 40, in connection with ultrasonic cleaning apparatus 1 shown in FIG. 2.

Figure 2:
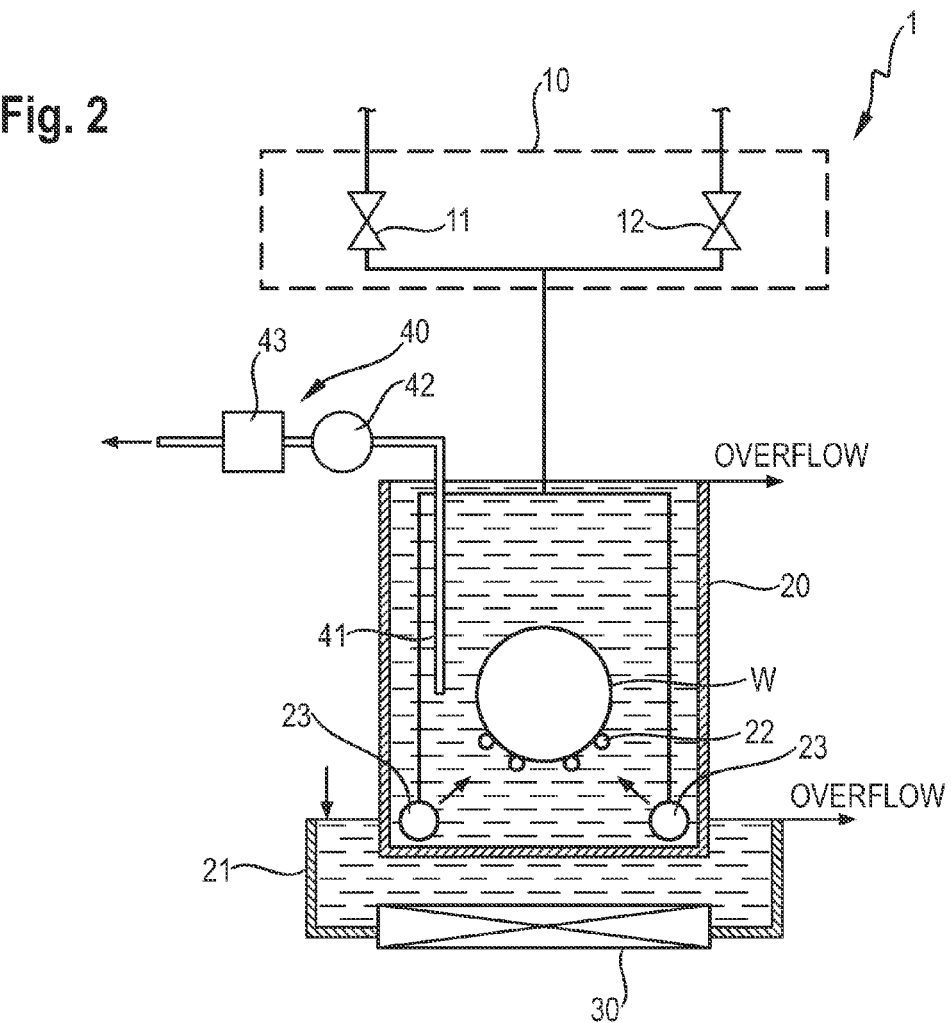
FIG. 2 is a schematic cross-sectional view showing a cleaning apparatus.

Here, as shown in FIG. 2, the ultrasonic cleaning apparatus 1 to which the calibration method according to the present invention is applied, includes a cleaning tank 20 for holding a cleaning liquid inside, such as ultrapure water, supply means 10 for supplying the cleaning liquid to cleaning tank 20, a coupling tank 21 for housing cleaning tank 20, irradiation means 30 for directing ultrasonic waves, installed at a bottom portion of coupling tank 21, and monitoring means 40 for monitoring a concentration of nitrogen dissolved in the cleaning liquid supplied into cleaning tank 20. Supply means 10 has a first supply valve 11 for supplying ultrapure water containing nitrogen gas dissolved therein to cleaning tank 20, and a second supply valve 12 for supplying degassed ultrapure water to cleaning tank 20.

First supply valve 11 is connected to a first tank, not illustrated. Ultrapure water containing nitrogen gas dissolved therein is stored in the first tank. Second supply valve 12 is connected to a device for producing degassed water, not illustrated. The ultrapure water is supplied to the device for producing degassed water, and the gas dissolved in the ultrapure water can be removed through a degassing membrane. The ultrapure water containing nitrogen gas dissolved therein and degassed ultrapure water are mixed when a pipe connected to first supply valve 11 and a pipe connected to second supply valve 12 are combined into a single pipe on a downstream side of first supply valve 11 and second supply valve 12. It is noted that a mixer tank (not illustrated) may be installed downstream of first supply valve 11 and second supply valve 12. In this case, ultrapure water containing nitrogen gas dissolved therein and degassed ultrapure water can be thoroughly mixed in the mixer tank.

The mixed ultrapure water then passes through the pipe connected to the downstream side of first supply valve 11 and second supply valve 12 described above and disposed within cleaning tank 20, and is supplied to a liquid introducing pipe 23. Liquid introducing pipe 23 is disposed near an outer peripheral end of a bottom surface of cleaning tank 20. By adjusting the valve position of each of first supply valve 11 and second supply valve 12, the ultrapure water to be introduced into cleaning tank 20 can be controlled with respect to the concentration of nitrogen dissolved therein and the amount of supply.

A plurality of nozzles, not illustrated, is disposed on liquid introducing pipe 23. Ultrapure water serving as the cleaning liquid is supplied from liquid introducing pipe 23 via the nozzles into cleaning tank 20. The nozzles are disposed at intervals from one another along a direction in which liquid introducing pipe 23 extends. The nozzles are also installed so as to spray the cleaning liquid toward substantially the center (a region where a wafer W to be cleaned is held) of cleaning tank 20.

A holding portion 22 for holding wafer W inside is disposed in cleaning tank 20. A semiconductor wafer, for example, can be used as wafer W. With wafer W being held inside cleaning tank 20 by holding portion 22, the cleaning liquid composed of the above-described mixed ultrapure water is supplied into cleaning tank 20 from liquid introducing pipe 23.

As described above, liquid introducing pipe 23 is disposed on a lower portion of cleaning tank 20 (a region situated near a bottom wall or situated on an outer peripheral portion of the bottom wall connecting the bottom wall and side walls). A prescribed amount of the cleaning liquid (mixed ultrapure water) is supplied from liquid introducing pipe 23 into cleaning tank 20. Cleaning tank 20 is filled with the cleaning liquid, and the amount of the cleaning liquid supplied is adjusted such that a prescribed amount of the cleaning liquid overflows from the top of cleaning tank 20.

In this way, wafer W is being dipped in the cleaning liquid inside cleaning tank 20, as shown in FIG. 2.

Coupling tank 21 is connected to a supply line (not illustrated) for a medium different from that of supply means 10 described above. Water serving as a medium is supplied from the supply line into coupling tank 21. At least the bottom wall of cleaning tank 20 described above is in contact with the water stored in coupling tank 21. A prescribed amount of water is continuously supplied also to coupling tank 21 from the supply line, thereby causing a certain amount of water to be overflowing from coupling tank 21.

Irradiation means 30 is installed to be connected to a bottom wall of coupling tank 21. Irradiation means 30 directs ultrasonic waves to the water inside coupling tank 21. The cleaning liquid and wafer W inside cleaning tank 20 are irradiated with the directed ultrasonic waves via the water inside coupling tank 21 and a portion of cleaning tank 20 in contact with the water (for example, the bottom portion).

Irradiation means 30 can generate ultrasonic waves having a frequency not less than 20 kHz and not more than 2 MHz and a watt density not less than 0.05 W/cm$^2$ and not more than 7.0 W/cm$^2$, for example. By thus irradiating the cleaning liquid and wafer W with ultrasonic waves, wafer W dipped in the cleaning liquid can be efficiently cleaned. Preferably, ultrasonic waves having a frequency range not less than 400 kHz and not more than 1 MHz are used as the ultrasonic waves directed from irradiation means 30.

Monitoring means 40 includes an extraction pipe 41 for extracting a prescribed amount of the cleaning liquid from inside of cleaning tank 20, a pump 42 connected to extraction pipe 41 for introducing the cleaning liquid into a dissolved nitrogen concentration meter 43, and dissolved nitrogen concentration meter 43 connected to the downstream side of pump 42. Measured data of the concentration of nitrogen dissolved in the cleaning liquid is output from dissolved nitrogen concentration meter 43 to a control device for the ultrasonic cleaning apparatus, an external display device, and the like. Any calibration device can be used as dissolved nitrogen concentration meter 43, for example, a measurement device can be used that introduces a dissolved gas component contained in a cleaning liquid into a receptor through a polymer membrane, and calculates the concentration of the gas component based on a change in thermal conductivity within this receptor.

Cleaning tank 20 is composed of, for example, quartz glass with a thickness of 3.0 mm. While cleaning tank 20 can have any shape, a square tank whose internal dimensions are 270 mm in width, 69 mm in length, and 270 mm in height, for example, is used as cleaning tank 20. In this case, cleaning tank 20 has a volume of 5 liters.

The thickness of a plate material made of quartz glass constituting the bottom wall of cleaning tank 20 is preferably adjusted, as appropriate, in accordance with the frequency of the ultrasonic waves emitted from irradiation means 30. For example, where the frequency of ultrasonic waves emitted from irradiation means 30 is 950 kHz, the thickness of the plate material constituting the bottom wall is preferably 3.0 mm. Where the frequency of ultrasonic waves emitted from irradiation means 30 is 750 kHz, the thickness of the plate material constituting the bottom wall is preferably 4.0 mm, for example.

The amount of the cleaning liquid (mixed ultrapure water) supplied to cleaning tank 20 from supply means 10 may be 5 liters/minute. The frequencies of ultrasonic waves directed from irradiation means 30 may be 950 kHz and 750 kHz as mentioned above, and the output thereof may be 1200 W (watt density: 5.6 W/cm$^2$). A vibrating plate of irradiation means 30 may have a radiation surface with a size of 80 mm×270 mm. Ultrasonic waves emitted from irradiation means 30 are directed to the entire bottom surface of cleaning tank 20.

The calibration method according to the present invention is applied to such ultrasonic cleaning apparatus 1. That is, referring to FIG. 1, in the calibration method according to the present invention, a step (S10) of determining a reference value of the concentration of dissolved nitrogen at the beginning of luminescence ($C_0$) is conducted first.

Figure 3:
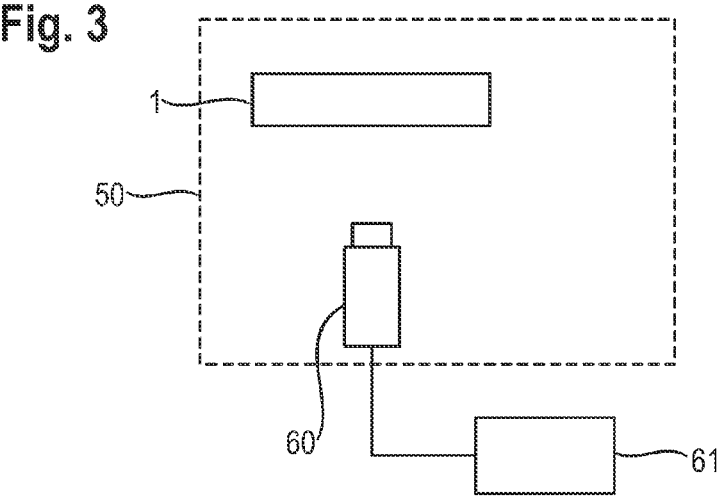
FIG. 3 is a schematic diagram showing an apparatus configuration when the calibration method is conducted.

At this step (S10), in connection with ultrasonic cleaning apparatus 1 as shown in FIG. 2, an image intensifier unit serving as a luminescence detecting device 60 and ultrasonic cleaning apparatus 1 are disposed inside a dark room 50, as shown in FIG. 3. Luminescence detecting device 60 is connected to an image processing device 61. Dissolved nitrogen concentration meter 43, having high measurement precision immediately after adjustment by the manufacturer, is installed in advance in ultrasonic cleaning apparatus 1. Using such a structure, in ultrasonic cleaning apparatus 1 installed inside dark room 50, the cleaning liquid was irradiated with ultrasonic waves while varying the concentration of nitrogen dissolved in the cleaning liquid, and the luminescence phenomenon (sonoluminescence) that occurred abruptly at a prescribed nitrogen concentration was observed.

Specifically, as shown in FIG. 3, ultrasonic cleaning apparatus 1 is disposed inside dark room 50 and luminescence detecting device 60 is disposed to face ultrasonic cleaning apparatus 1 in dark room 50. A dissolved nitrogen concentration meter immediately after adjustment by the manufacturer is used as dissolved nitrogen concentration meter 43 of ultrasonic cleaning apparatus 1. Then, in connection with ultrasonic cleaning apparatus 1, the concentration of nitrogen dissolved in the cleaning liquid is varied while the cleaning liquid is being irradiated with ultrasonic waves from irradiation means 30, thereby determining a concentration of dissolved nitrogen at which abrupt luminescence occurs (hereinafter referred to as a dissolved nitrogen concentration reference value at the beginning of luminescence) by means of measurement using dissolved nitrogen concentration meter 43.

The image intensifier unit (an ultraweak light sensing and multiplying unit) used as luminescence detecting device 60 is a device that senses and multiplies ultraweak light to obtain an image with a contrast. Specifically, a unit employing an image intensifier (V4435U-03) manufactured by Hamamatsu Photonics can be used as such a unit. This unit uses Cs—Te as material of the photoelectric surface material, has sensitivity wavelengths ranging from 160 to 320 nm, and has a maximum sensitivity wavelength of 250 nm. It is believed that luminescence produced when water is irradiated with ultrasonic waves is due to hydroxy radicals (OH radicals) generated by the decomposition of water, and the luminescence has a wavelength near 309 nm in the ultraviolet region. Therefore, the image intensifier unit having the photoelectric surface material (Cs—Te), which has the above-mentioned wavelength in the sensitivity wavelength range, was herein used. A photomultiplier tube may also be used as luminescence detecting device 60.

The frequency of ultrasonic waves directed at this time was set to 950 kHz. The output of the ultrasonic waves was 1200 W (watt density: 5.6 W/cm$^2$), as described above. The luminescence phenomenon was then observed for the cleaning liquid while gradually increasing the concentration of dissolved nitrogen. The amount of the cleaning liquid supplied was 5 L/minute.

Figure 4:
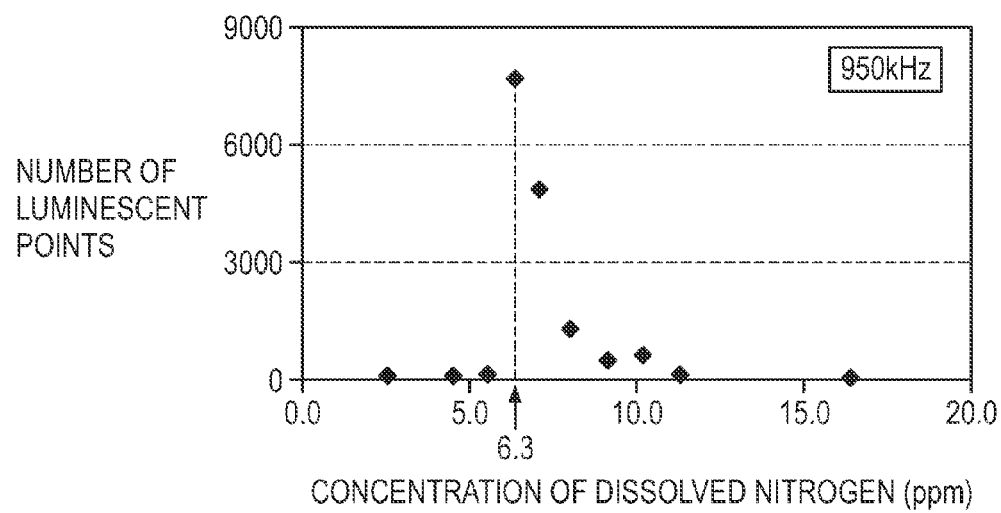
FIG. 4 is a graph showing measured results.

Specifically, the concentration of dissolved nitrogen was gradually increased from 2.5 ppm to 16.4 ppm. Consequently, the luminescence phenomenon abruptly occurred in the cleaning liquid when the concentration of dissolved nitrogen was near 6.3 ppm. The inventors' experiment confirmed that with apparatus conditions being kept substantially constant, the luminescence phenomenon was observed with good reproducibility when the concentration of dissolved nitrogen was near 6.3 ppm. FIG. 4 shows observation results plotted on a graph. In FIG. 4, the horizontal axis represents the concentration of nitrogen dissolved in the cleaning liquid. The horizontal axis shows concentrations of dissolved nitrogen in the unit ppm. The vertical axis represents the number of measured luminescent points. The number of luminescent points is calculated by processing image data of the luminescence phenomenon measured by luminescence detecting device 60 at image processing device 61. As seen from FIG. 4, where the frequency of the ultrasonic waves is 950 kHz, the concentration of dissolved nitrogen at which the number of luminescent points sharply increases is 6.3 ppm, as described above. The inventors also confirmed that such a luminescence phenomenon was observed with good reproducibility at the above-described concentration of dissolved nitrogen near 6.3 ppm. Therefore, where the frequency of the ultrasonic waves is 950 kHz, the dissolved nitrogen concentration meter may be calibrated as described below, by setting the concentration of dissolved nitrogen at which abrupt luminescence occurs to 6.3 ppm as the concentration of nitrogen dissolved in the cleaning liquid is gradually increased.

Figure 5:
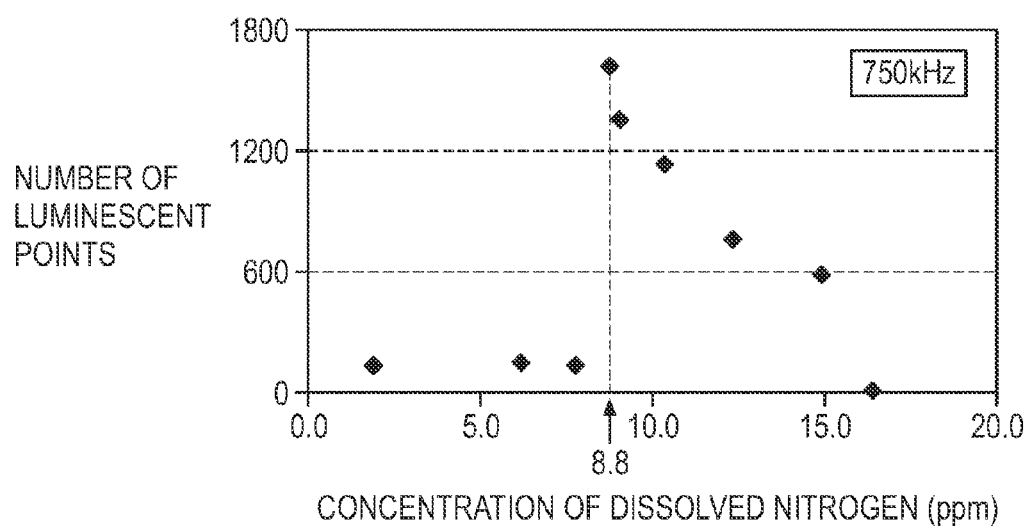
FIG. 5 is a graph showing measured results.

Also for the case where the frequency of the ultrasonic waves used was set to 750 kHz, the same observations were made by gradually increasing the concentration of dissolved nitrogen from 1.9 ppm to 14.9 ppm. As a result, where the frequency of the ultrasonic waves was 750 kHz, the concentration of dissolved nitrogen at which the luminescence phenomenon abruptly occurs was found to be 8.8 ppm. FIG. 5 shows observation results plotted on a graph. In FIG. 5, the horizontal axis represents the concentration of nitrogen dissolved in the cleaning liquid, as in FIG. 4. The horizontal axis shows concentrations of dissolved nitrogen in the unit ppm. The vertical axis represents the number of measured luminescent points. As seen from FIG. 5, where the frequency of the ultrasonic waves is 750 kHz, the concentration of dissolved nitrogen at which the number of luminescent points sharply increases is 8.8 ppm, as described above. The inventors further confirmed that also for the case where ultrasonic waves with a frequency of 750 kHz were used as described above, the luminescence phenomenon was observed with good reproducibility. Therefore, where the frequency of the ultrasonic waves is 750 kHz, the dissolved nitrogen concentration meter may be calibrated as described below, by setting the concentration of dissolved nitrogen at which abrupt luminescence occurs to 8.8 ppm as the concentration of nitrogen dissolved in the cleaning liquid is gradually increased.

In this way, the concentration of dissolved nitrogen at which the luminescence phenomenon (sonoluminescence) abruptly begins when the concentration of nitrogen dissolved in the cleaning liquid is gradually increased is determined as a dissolved nitrogen concentration reference value at the beginning of luminescence ($C_0$). The concentration of dissolved nitrogen at the beginning of luminescence is defined herein as the concentration of dissolved nitrogen at which the luminescence (sonoluminescence) phenomenon abruptly occurs when the concentration of nitrogen dissolved in the solution that is being irradiated with ultrasonic waves is gradually increased. The dissolved nitrogen concentration reference value at the beginning of luminescence is also defined as the concentration of dissolved nitrogen at the beginning of luminescence (namely, the concentration of dissolved nitrogen at which the luminescence (sonoluminescence) phenomenon abruptly occurs when the concentration of nitrogen dissolved in the solution that is being irradiated with ultrasonic waves is gradually increased), and as being measured, with the structure of the apparatus to be measured being fixed under certain conditions, by using a dissolved nitrogen concentration meter having accurate measurement precision, such as one immediately after adjustment by the manufacturer. Examples of conditions for the apparatus include the ultrasonic frequency, the ultrasonic intensity, the design of the water tank holding the solution, the amount of solution supplied, etc.

Next, as shown in FIG. 1, a step of determining a dissolved nitrogen concentration at the beginning of luminescence ($C_A$) with the dissolved nitrogen concentration meter to be calibrated is conducted. Specifically, ultrasonic cleaning apparatus 1 is prepared having the same structure as that of the ultrasonic cleaning apparatus used in the above-described step (S10), in which the dissolved nitrogen concentration meter to be calibrated (for example, a dissolved nitrogen concentration meter after about 5 months from adjustment by the manufacturer) is installed. Ultrasonic cleaning apparatus 1 including such a dissolved nitrogen concentration meter to be calibrated is incorporated into a measurement system as shown in FIG. 3. The luminescence phenomenon was then observed while varying the concentration of dissolved nitrogen, as in the step (S10). Here, the concentration of dissolved nitrogen is measured using the dissolved nitrogen concentration meter to be calibrated. In this way, the concentration of dissolved nitrogen at the time when the luminescence phenomenon begins to abruptly occur (dissolved nitrogen concentration at the beginning of luminescence ($C_A$)) is measured. The frequency of the ultrasonic waves used herein is the same as that of the ultrasonic waves used in the above-described step (S10). Specifically, the frequency of the ultrasonic waves is 950 kHz. In this case, the dissolved nitrogen concentration at the beginning of luminescence ($C_A$) (namely, a measured value of the concentration of dissolved nitrogen at the beginning of luminescence) was 5.0 ppm.

Next, a step (S30) of calibrating the dissolved nitrogen concentration meter shown in FIG. 1 is conducted. Specifically, a calibration coefficient for calibrating a measured value obtained from the dissolved nitrogen concentration meter to be calibrated is found from the dissolved nitrogen concentration reference value at the beginning of luminescence ($C_0$) and the dissolved nitrogen concentration at the beginning of luminescence ($C_A$) described above. That is, a concentration of dissolved nitrogen after calibrating the measured value using the calibration coefficient (accurate after calibration) ($C_{cal}$) can be found from a measured value of concentration of dissolved nitrogen before calibration ($C_{meas}$)) and a ratio of $C_0$ to $C_A$ ($C_0/C_A$) measured in the above-described step (S10) and step (S20), in accordance with the following equation:

$$C_{cal} = C_{meas} \times C_0/C_A$$

Since $C_0$ is 6.3 ppm and $C_A$ is 5.0 ppm as described above, the equation shown above is expressed as follows:

$$C_{cal} = C_{meas} \times 6.3/5.0$$

Accordingly, an accurate concentration of dissolved nitrogen can be found by converting a measured value obtained from the dissolved nitrogen concentration meter in accordance with such an equation including the calibration coefficient. For example, with a control device that has received data of the measured value from the dissolved nitrogen concentration meter, processing may be performed in which an accurately calculated value of concentration of dissolved nitrogen is calculated by multiplying the measured value by the calibration coefficient as described above, and the calculated value is output to an external display device or the like.

Second Embodiment

Figure 6:
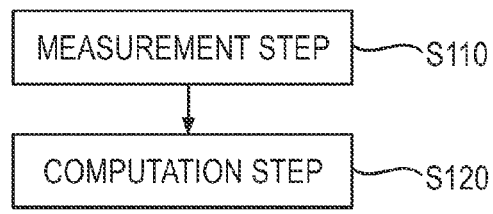
FIG. 6 is a flowchart for explaining a method for measuring a dissolved nitrogen concentration according to an embodiment of the present invention.
Figure 7:
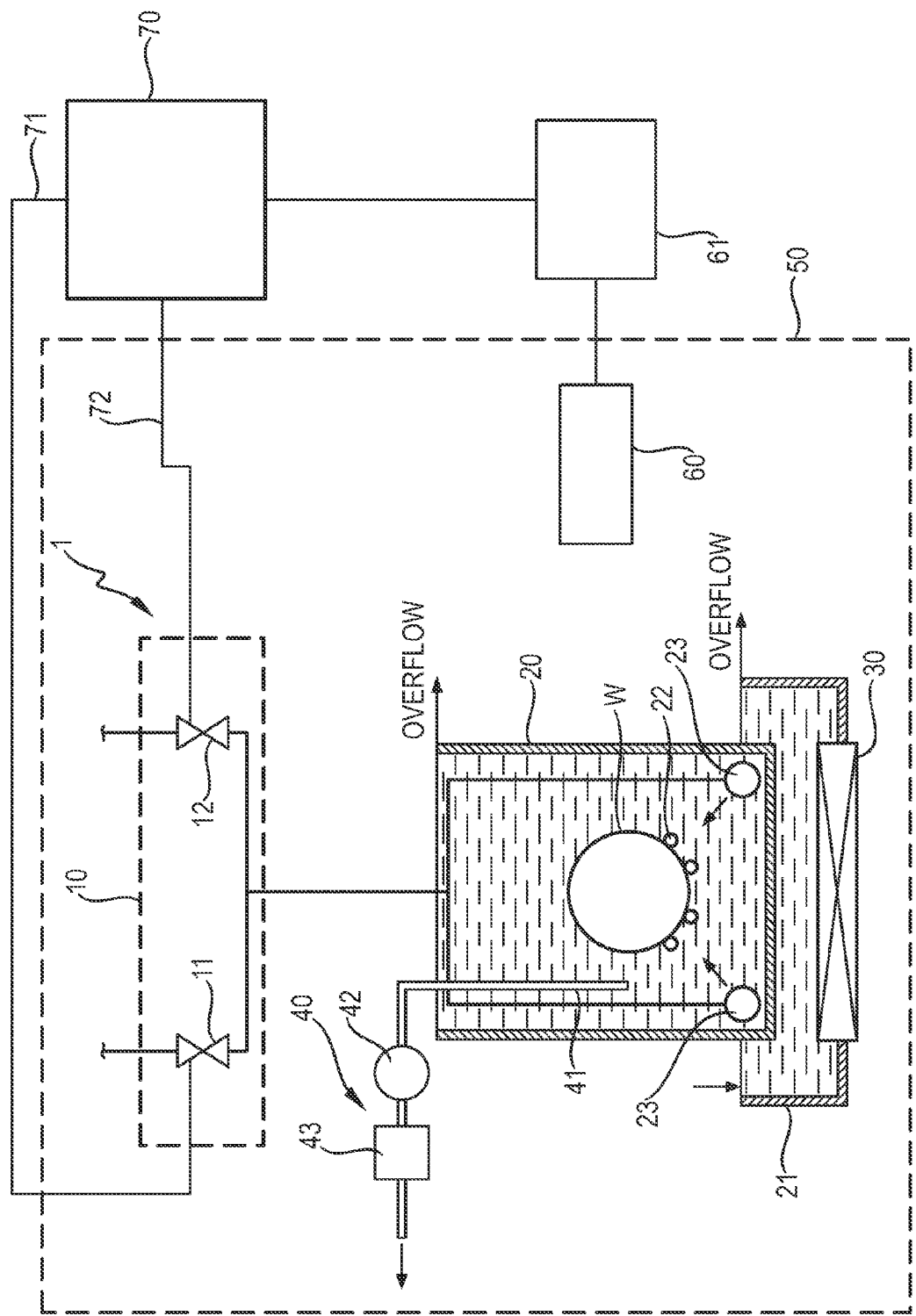
FIG. 7 is a schematic diagram of a cleaning apparatus that utilizes the measurement method shown in FIG. 6.

Referring to FIGS. 6 and 7, a method for measuring the concentration of dissolved nitrogen according to the present invention and a cleaning apparatus according to the present invention will be described.

As shown in FIG. 6, in the method for measuring the concentration of dissolved nitrogen according to the present invention, a measurement step (S110) is conducted first. Specifically, in the cleaning apparatus having an apparatus structure as shown in FIG. 7, the luminescence phenomenon is observed for a cleaning liquid in cleaning tank 20 of ultrasonic cleaning apparatus 1. As shown in FIG. 7, the cleaning apparatus according to the present invention includes ultrasonic cleaning apparatus 1, dark room 50, luminescence detecting device 60, image processing device 61, and control device 70. As shown in FIG. 7, ultrasonic cleaning apparatus 1 is disposed inside dark room 50. Luminescence detecting device 60 is also disposed to face cleaning tank 20 of ultrasonic cleaning apparatus 1. Luminescence detecting device 60 is connected to image processing device 61. Image processing device 61 is in turn connected to control device 70. Control device 70 is connected to first supply valve 11 and second supply valve 12 constituting supply means 10 of ultrasonic cleaning apparatus 1, via wires 71, 72, respectively.

In such an apparatus structure, ultrasonic waves having a prescribed frequency (for example, 950 kHz) are applied to the cleaning liquid from irradiation means 30 while supplying the cleaning liquid to ultrasonic cleaning apparatus 1. In this state, luminescence in the cleaning liquid is observed with luminescence detecting device 60. Measured data (image data) observed with luminescence detecting device 60 is processed at image processing device 61, whereby the number of luminescent points is derived.

Next, a computation step (S120) shown in FIG. 6 is conducted. Specifically, from the number of luminescent points found in the step (S110), the concentration of nitrogen dissolved in the cleaning liquid is found based on a correlation between the concentration of dissolved nitrogen and the number of luminescent points as shown in FIG. 4 or 5, which is associated with the ultrasonic waves of the frequency used in the step (S110). For example, where the frequency at the ultrasonic waves used in the above-described step (S110) is 950 kHz, the correlation between the concentration of dissolved nitrogen and the number of luminescent points as shown in FIG. 4 is obtained in advance. Where the frequency of the ultrasonic waves used in the above-described step (S110) is 750 kHz, the correlation between the concentration of dissolved nitrogen and the number of luminescent points as shown in FIG. 5 is obtained in advance.

It is noted that the range of concentrations in which the concentration of dissolved nitrogen can be found by the above-described method is a range of concentrations of dissolved nitrogen in which the relation between the number of luminescent points and the concentration of dissolved nitrogen is a one-to-one correspondence. For example, in the case of the correlation shown in FIG. 4 (where the frequency of ultrasonic waves is 950 kHz), the concentration of nitrogen dissolved in the cleaning liquid can be determined with respect to a range of concentrations of dissolved nitrogen not less than 6.3 ppm and not more than 9 ppm, by using the above-described measurement method according to the present invention. In the case of the correlation shown in FIG. 5 (where the frequency of ultrasonic waves is 750 kHz), the concentration of nitrogen dissolved in the cleaning liquid can be determined with respect to a range of concentrations of dissolved nitrogen not less than 8.8 ppm and not more than 15.0 ppm, by using the above-described measurement method. In this way, with respect to a range where the relation between the number of luminescent points and the concentration of dissolved nitrogen is on a one-to-one basis (for example, has a proportional relation), the concentration of nitrogen dissolved in the cleaning liquid can be found from a measured result of the number of luminescent points.

With respect to the relation between the number of luminescent points and the concentration of dissolved nitrogen in the graph shown in FIG. 4 or 5, precision can be improved by increasing the number of levels of concentrations of dissolved nitrogen at which measurements are conducted to increase the number of items of data. Alternatively, a relational expression between the number of luminescent points and the concentration of dissolved nitrogen may be found approximately from a prescribed number of items of experimental data, and the concentration of dissolved nitrogen may be found from the number of luminescent points based on the relational expression.

Where the concentration of dissolved nitrogen is found by computation in the computation step (S120), the concentration of nitrogen dissolved in the cleaning liquid in ultrasonic cleaning apparatus 1 can also be controlled to give a prescribed value (set value). For example, the above-described step (S120) may be conducted at control device 70 shown in FIG. 7 to find a current value of concentration of dissolved nitrogen, which is subsequently compared with the set value, and first supply valve 11 and second supply valve 12 may be controlled by control device 70 so as to reduce the difference. In this way, feedback control can be performed so as to make the concentration of nitrogen dissolved in the cleaning liquid in ultrasonic cleaning apparatus 1 approach the set value.

In principle, the phenomenon in which abrupt luminescence occurs at a prescribed concentration of a dissolved gas as described above is similarly produced also in the case where a gas other than nitrogen, for example, a molecular gas such as oxygen, hydrogen, or carbon dioxide, or a noble gas such as helium or argon, is dissolved in the liquid. Therefore, the dissolved gas to be measured by the present invention is not limited to nitrogen, and the present invention is also applicable to cases where other gases are dissolved in the liquid.

Characteristic features of the present invention will now be listed although they may partly overlap with the embodiments described above.

A calibration method according to an embodiment of the invention is a calibration method for calibrating dissolved nitrogen concentration meter 43 serving as a measurement device for measuring a concentration of a gas dissolved in a liquid, which includes the following steps. That is, the step (S10) of varying the concentration of the gas (nitrogen) dissolved in the liquid (cleaning liquid), and predetermining, as a reference concentration (dissolved nitrogen concentration reference value at the beginning of luminescence ($C_0$)), a concentration of the gas at which an intensity of luminescence produced when the liquid is irradiated with ultrasonic waves shows a peak, is conducted. Next, the step (S20) of measuring the concentration of nitrogen in the cleaning liquid with the measurement device to be calibrated (dissolved nitrogen concentration meter 43) when the intensity of the luminescence shows a peak by irradiating the liquid with ultrasonic waves while varying the concentration of the gas in the liquid, to determine a measured value of the concentration of nitrogen (dissolved nitrogen concentration at the beginning of luminescence ($C_A$)), is conducted. The step (S30) of calibrating the measurement device to be calibrated (dissolved nitrogen concentration meter 43) based on the measured value (dissolved nitrogen concentration at the beginning of luminescence ($C_A$)) and the reference concentration (dissolved nitrogen concentration reference value at the beginning of luminescence ($C_0$)) is conducted. In the predetermining step (S10) described above, any method capable of accurately measuring the concentration can be used as a method for measuring the concentration of the gas dissolved in the liquid. For example, in the predetermining step (S10) described above, a dissolved nitrogen concentration meter of the same type as dissolved nitrogen concentration meter 43 to be measured, having the setting at the time of shipment from the factory (namely, a dissolved nitrogen concentration meter capable of accurate measurement that has just been subjected to adjustment by the manufacturer), may be used.

In this way, dissolved nitrogen concentration meter 43 can be calibrated easily and accurately by utilizing sonoluminescence.

In the above-described calibration method, in the calibration step (S30), a correction coefficient (ratio of $C_0$ to $C_A$ ($C_0/C_A$)) for correcting data output from dissolved nitrogen concentration meter 43 may be determined based on the measured value (concentration of dissolved nitrogen at the beginning of luminescence ($C_A$)) and the reference concentration (dissolved nitrogen concentration reference value at the beginning of luminescence ($C_0$)). In this case, an accurate value of the concentration of a gas dissolved in the liquid can be obtained by multiplying the data output from the measurement device by the correction coefficient.

In the above-described calibration method, the above-described liquid may be water. Water is utilized as a medium in various types of treatment, and a calibration method for a measurement device for measuring the concentration of a gas dissolved in water finds a wide range of applications, and therefore, the present invention can be effectively utilized.

In the above-described calibration method, the intensity of luminescence is measured using either one of an image intensifier and a photomultiplier tube. In this case, even when the intensity of luminescence produced when the cleaning liquid is irradiated with ultrasonic waves is weak, the intensity of the luminescence can be measured relatively accurately.

In the above-mentioned calibration method, the gas may be nitrogen. In case of nitrogen, the concentration as dissolved in the liquid (cleaning liquid) is difficult to measure stably with good precision, as compared with other gases such as oxygen. According to the present invention, the measurement precision of the dissolved concentration can be maintained high, thus resulting in a particularly remarkable effect of the present invention if the dissolved gas is nitrogen.

In the above-described calibration method, the liquid may be a cleaning liquid for cleaning a semiconductor substrate. The measurement device may be included in the cleaning apparatus (ultrasonic cleaning apparatus 1) for cleaning the semiconductor substrate (wafer W), as shown in FIG. 2. In this case, the measurement precision of the measurement device can be maintained high, by applying the calibration method according to the present invention to calibration of the measurement device (dissolved nitrogen concentration meter 43) for measuring the concentration of a prescribed gas dissolved in the cleaning liquid in ultrasonic cleaning apparatus 1.

A measurement method according to an embodiment of the invention is a measurement method for measuring the concentration of a gas (for example, nitrogen) dissolved in a liquid (cleaning liquid), which includes the following steps. That is, a step (measurement step (S110)) of measuring an intensity of luminescence produced by irradiating the liquid (cleaning liquid) to be measured with ultrasonic waves by way of a luminescence intensity measuring device (luminescence detecting device 60) to obtain a measured value of the intensity of the luminescence (the number of luminescent points) is conducted. Next, a step (computation step (S120)) of deriving the concentration of the gas dissolved in the cleaning liquid from the measured value of the intensity of the luminescence (the measured data of the number of luminescent points) based on a previously found correlation between the concentration of the gas (nitrogen) dissolved in the liquid (cleaning liquid) as shown in FIG. 4 or 5 and the intensity of the luminescence (for example, the number of luminescent points) produced when the liquid (cleaning liquid) is irradiated with ultrasonic waves is conducted.

In this way, with respect to the range of concentrations of the gas having the correlation shown in FIG. 4, FIG. 5, or the like between the intensity of the luminescence (data of the number of luminescent points) due to sonoluminescence in the liquid (cleaning liquid) and the concentration of the gas (nitrogen) dissolved in the liquid (cleaning liquid), the concentration of the gas dissolved (concentration of dissolved nitrogen) in the liquid (cleaning liquid) can be readily found from the intensity of the luminescence (data of the number of luminescent points).

In the above-described measurement method, the derived range of concentrations of the gas (nitrogen) is preferably in a range in which the correlation shown in FIG. 4 or 5 shows a one-to-one correspondence between the concentration of the gas (concentration of dissolved nitrogen) and the intensity of the luminescence (the number of luminescent points). In this case, the concentration of the gas dissolved (concentration of nitrogen dissolved) in the liquid (cleaning liquid) can be reliably found from the intensity of the luminescence (data of the number of luminescent points).

A cleaning apparatus according to an embodiment of the invention is an apparatus for cleaning wafer W shown in FIG. 7 using the above-described measurement method, which includes cleaning tank 20, the ultrasonic generating unit (irradiation means 30), the luminescence intensity measuring device (luminescence detecting device 60), and the processing unit (control device 70). The cleaning tank 20 holds the cleaning liquid for cleaning the substrate (wafer W). The ultrasonic generating unit (irradiation means 30) is for irradiating the cleaning liquid with ultrasonic waves and generates ultrasonic waves. Irradiation means 30 is connected to cleaning tank 20 via media capable of transmitting ultrasonic waves to the cleaning liquid in cleaning tank 20 (water held in coupling tank 21 and the bottom wall of cleaning tank 20). The luminescence intensity measuring device (luminescence detecting device 60) measures the intensity of luminescence produced when the cleaning liquid is irradiated with ultrasonic waves. The processing unit (control device 70) derives the concentration of a dissolved gas (concentration of dissolved nitrogen) in the cleaning liquid from a measured value of the intensity of the luminescence measured by luminescence detecting device 60 (the number of luminescent points computed by image processing device 61) and from the previously found correlation as shown in FIG. 4 or 5 between the concentration of the dissolved gas (concentration of dissolved nitrogen) in the cleaning liquid and the intensity of the luminescence (the number of luminescent points).

In this way, the concentration of the gas (nitrogen) dissolved in the cleaning liquid can be accurately measured from the intensity of the luminescence (the number of luminescent points) due to sonoluminescence, thus enabling the nitrogen concentration in the cleaning liquid to be accurately controlled based on the measured result. Therefore, a characteristic (cleaning capability) of the cleaning liquid affected by the nitrogen concentration can be accurately grasped, and the characteristic of the cleaning liquid can be kept satisfactory by adjusting the cleaning liquid such that the concentration of dissolved nitrogen is within an appropriate range.

The above-described cleaning apparatus may further include a supply unit (supply means 10) for supplying the cleaning liquid to cleaning tank 20. The processing unit (control device 70) may control the concentration of the above-mentioned gas (concentration of nitrogen dissolved) in the cleaning liquid supplied from supply means 10, in accordance with the derived concentration of the gas (concentration of dissolved nitrogen). In this case, the concentration of nitrogen in the cleaning liquid can be adjusted so as to improve the characteristic (cleaning capability) of the cleaning liquid affected by the nitrogen concentration. Consequently, a cleaning apparatus exhibiting improved cleaning capability can be realized.

It should be understood that the embodiments disclosed herein are illustrative and non-restrictive in every respect. The scope of the present invention is defined by the terms of the claims, rather than by the foregoing description, and is intended to include any modifications within the scope and meaning equivalent to the terms of the claims.

INDUSTRIAL AVAILABILITY

Embodiments of the invention can be advantageously applied, in particular, to a cleaning apparatus and the like using a liquid, in which the concentration of a gas dissolved in the liquid needs to be measured.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

LIST OF REFERENCE CHARACTERS

1: ultrasonic cleaning apparatus
10: supply means
11: first supply valve
12: second supply valve
20: cleaning tank
21: coupling tank
22: holding portion
23: liquid introducing pipe
30: irradiation means
40: monitoring means
41: extraction pipe
42: pump
43: dissolved nitrogen concentration meter
50: dark room
60: luminescence detecting device
61: image processing device
70: control device
71, 72: wire
W: wafer

What is claimed is:

1. A calibration method for calibrating a measurement device for measuring a concentration of a gas dissolved in a liquid, the method comprising:
   varying the concentration of the gas dissolved in the liquid, and predetermining, as a reference concentration, a concentration of the gas at which an intensity of luminescence produced when the liquid is irradiated with ultrasonic waves shows a peak;
   irradiating the liquid with ultrasonic waves while varying the concentration of the gas in the liquid and measuring, using the measurement device, as a measured value, a concentration of the gas in the liquid when the intensity of the luminescence shows a peak; and
   calibrating the measurement device based on the measured value and the reference concentration.

2. The calibration method according to claim 1, wherein the liquid is water.

3. The calibration method according to claim 1, wherein the intensity of the luminescence is measured using at least one of an image intensifier and a photomultiplier tube.

4. The calibration method according to claim 1, wherein the gas is nitrogen.

5. The calibration method according to claim 1, wherein the liquid is a cleaning liquid for cleaning a semiconductor substrate, and the measurement device is included in a cleaning apparatus configured to clean the semiconductor substrate.

6. A measurement method for measuring a concentration of a gas dissolved in a liquid, the method comprising:
   irradiating the liquid with ultrasonic waves and measuring, using a luminescence intensity measuring device, an intensity of luminescence produced to obtain a measured value of the intensity of the luminescence; and
   deriving the concentration of the gas from the measured value of the intensity of the luminescence based on a predetermined correlation between the concentration of the gas dissolved in the liquid and the intensity of the luminescence produced when the liquid is irradiated with ultrasonic waves.

7. An apparatus for cleaning a substrate comprising:
   a cleaning tank configured to hold a cleaning liquid for cleaning the substrate;
   an ultrasonic generating unit configured to irradiate the cleaning liquid with ultrasonic waves, the ultrasonic generating unit being connected to the cleaning tank via a medium capable of transmitting the ultrasonic waves to the cleaning liquid in the cleaning tank;
   a luminescence intensity measuring device configured to measure, as a measured value, an intensity of luminescence produced when the cleaning liquid is irradiated with the ultrasonic waves; and
   a processing unit configured to derive a concentration of the gas dissolved in the cleaning liquid from the measured value and a predetermined correlation between the concentration of the gas dissolved in the cleaning liquid and the intensity of the luminescence.

* * * * *